United States Patent [19]

Christidis et al.

[11] 4,088,657

[45] May 9, 1978

[54] PROCESS FOR MANUFACTURING N-ACYL DERIVATIVES OF GLYCINES α-SUBSTITUTED BY RADICALS OF AROMATIC NATURE AND NOVEL PRODUCTS THEREOF

[75] Inventors: Yani Christidis, Paris; Alain Schouteeten, Villiers Le Bel, both of France

[73] Assignee: Nobel Hoechst Chimie, Puteaux, France

[21] Appl. No.: 722,286

[22] Filed: Sep. 10, 1976

[30] Foreign Application Priority Data

Sep. 12, 1975 France .............................. 75 28152

[51] Int. Cl.$^2$ .................. C07D 333/24; C07C 101/42
[52] U.S. Cl. ......................... 260/332.2 A; 260/518 R; 260/518 A; 260/534 M
[58] Field of Search ............... 260/534 M, 332.2 A, 260/518 R, 518 A

[56] References Cited

U.S. PATENT DOCUMENTS 3,920,730  11/1975  Gleason ...................... 260/332.2 A

*Primary Examiner*—Alan M. Siegel
*Attorney, Agent, or Firm*—Karl W. Flocks

[57] ABSTRACT

This is an improved process of manufacturing N-acyl derivatives of glycines α-substituted by radicals with an aromatic nature by condensation of the addition product of glyoxylic acid and an amide, with an aromatic compound. In a first stage, the reaction is carried out at low temperature, in a concentrated sulfuric medium, of an aliphatic nitrile of the formula R—C≡N in which R is a radical selected from the group of substituted and unsubstituted, saturated and unsaturated alkyl radicals, with a concentrated aqueous solution of glyoxylic acid. Then in a second stage, the mixture obtained is condensed also at low temperature with a compound of aromatic nature not including a hydroxyl group and having at least one substitutable free hydrogen, and the resulting product is collected. The concentrated sulfuric acid may be supplemented with acetic acid during the second stage. A surface active agent may be also added in this stage. The products are valuable intermediates for the preparation of semi-synthetic penicillins.

6 Claims, No Drawings

PROCESS FOR MANUFACTURING N-ACYL DERIVATIVES OF GLYCINES α-SUBSTITUTED BY RADICALS OF AROMATIC NATURE AND NOVEL PRODUCTS THEREOF

BACKGROUND OF THE INVENTION

1. Field of the Invention

The present invention relates to a process for manufacturing N-acyl derivatives of glycines α-substituted by non-hydroxylated radicals of aromatic nature and the novel products resulting therefrom.

2. Description of the Prior Art

Certain glycines (or α-aminoacetic acids) substituted at the α position by non-hydroxylated radicals of aromatic nature, such as phenylglycine or 2-amino 2-phenyl acetic acid, thienylglycine or 2-amino 2-thienyl acetic acid, etc., are used among others as intermediates for the preparation of semi-synthetic penicillins. For this purpose, whether for the separation of the enantiomorphs or for reaction with penicillins, the —NH₂ group has to be protected by means of a group which is subsequently easily hydrolysable, for example an acyl group: the N-acyl derivatives of glycines α-substituted by radicals with an aromatic nature therefore constitute valuable intermediate products in the preparation of semi-synthetic penicillins. They are customarily obtained by acylation of the corresponding glycines, themselves prepared by the conventional methods of amino acid synthesis.

Among these methods, that of STRECKER and its modification, the method of BUCHERER, have been used for a long time. They consist essentially of reacting an aldehyde, in the first case, with an alkali cyanide and ammonia to obtain an α-aminonitrile, and in the second case, with an alkali cyanide and ammonium carbonate to obtain a hydantoin, this nitrile or this hydantoin then being hydrolysed in an acid medium (ULLMANNS ENCYKLOPADIE DER TECHNISCHEN CHEMIE — vol. 3 p. 507). They have the drawback of being rather long and complicated and especially of using as a starting material an aromatic aldehyde, which is an expensive substance.

Recently it has been proposed to prepare N-acyl derivatives of glycines α-substituted by radicals of an aromatic nature by condensing in an acetic medium, in the presence of sulfuric acid, aromatic compounds, substituted or not, with adduct products of glyoxylic acid and aromatic amides (D. BEN ISHAI, I. SATATI and Z. BERLER, J.C.S. Chem. Comm. No. 9 — July 5, 1975 — p. 349), the latter being themselves obtained by the action in an organic solvent medium of glyoxylic acid in the form of the hydrate on aromatic amides (U. ZOLLER and D. BEN ISHAI — Tetrahedron — vol. 31 p. 863–866 (1975)). This process enables N-acyl arylglycines to be obtained with satisfactory yields but has a certain number of drawbacks:

the aromatic amides are not manufactured industrially, the acyl residue obtained in utilising them and which disappears in the course of the subsequent utilisation of the N-acyl derivative is unnecessarily heavy and expensive.

the glyoxylic acid in the form of hydrate is no longer an industrial product, it is deliquescent and it is also expensive.

However, it is not possible to use this process with aliphatic amides of low molecular weight and aqueous solutions of glyoxylic acid since the adduct product, glyoxylic acid-aliphatic amide, is much more difficult to prepare and to isolate than the adduct product, glyoxylic acid-aromatic amide.

OBJECTS AND GENERAL DESCRIPTION OF THE INVENTION

It is an object of the present invention to provide a process for manufacturing N-acyl derivatives of glycines α-substituted by radicals of aromatic nature which overcomes the abovementioned drawbacks.

It is another object of the invention to provide novel products obtained by the latter process.

Applicant has found that it is possible to prepare easily glycines α-substituted by non-hydroxylated radicals of aromatic nature, by first reacting an aliphatic nitrile in a sulfuric medium with a concentrated aqueous solution of glyoxylic acid so as to form a carboxamido glycolic acid intermediately, and then condensing said carboxamido glycolic acid without isolating it, in the same medium or after the addition of acetic acid, with a compound of aromatic nature, non-hydroxylated, but having possibly other substituents.

If the nitriles used are represented by the formula R—C≡N, in which R is a saturated or unsaturated alkyl radical, possibly substituted, the reaction with glyoxylic acid of this nitrile leads apparently by hydrolysis and then by condensation to the corresponding carboxamido glycolic acid as represented by:

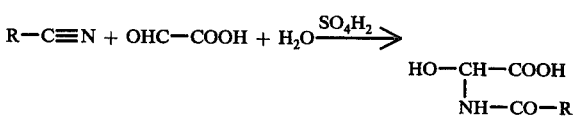

this carboxamido glycolic acid is then condensed with the compound of aromatic nature; this reaction in the simple case of benzene can be represented as follows:

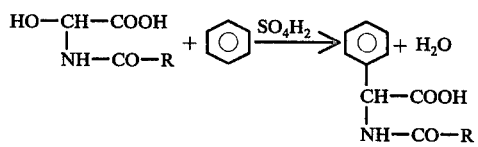

According to the invention, a nitrile R—C≡N, where R has the above-indicated signification, is reacted at low temperature, in a sulfuric medium, with a concentrated aqueous solution of glyoxylic acid; the resulting mixture which already contains sulfuric acid is condensed, also at low temperature, as is or possibly after the addition of acetic acid, without isolating the carboxamido glycolic acid, with a non-hydroxylated compound of aromatic nature.

The reaction of the glyoxylic acid with the aliphatic nitrile is carried out preferably at a temperature below 30° C and the condensation of the product of this reaction with the compound of aromatic nature preferably at a temperature below 35° C.

The nitriles usable for the preparation of the carboxamido glycolic acid are those of the formula R—C≡N, in which R has the above-indicated signification. It is advantageous to use saturated or unsaturated, possibly substituted aliphatic nitriles, comprising not more than four carbon atoms.

Among these nitriles may be mentioned acetonitrile, chloracetonitrile, propionitrile, acrylonitrile and butyronitrile.

It goes without saying that when an unsaturated nitrile is used, its polymerisation in the course of the various reactions should be prevented by means of a suitable polymerisation inhibitor, for example a copper salt.

The compounds of aromatic nature usable in the process according to the invention are all compounds comprising one or several nuclei of aromatic nature, possibly bearing other substituents than hydroxyls, provided that they include at least one free H capable of reacting with the carboxamido glycolic acid.

Of course, this reaction is carried out all the more easily as the free position will not undergo steric hindrance due to the existance of bulky substituents on neighbouring positions.

As the compound of aromatic nature it is possible to use advantageously benzene and its alkyl derivatives such as toluene and the xylenes, their halogen derivatives such as o-chlorobenzene, their nitro derivatives, thiophene and its substituted derivatives.

The compound of aromatic nature is used in excess with respect to the glyoxylic acid and the nitrile; this excess can reach 500%.

The reaction medium is constituted by concentrated sulfuric acid, preferably 96% sulfuric acid. Although the whole operation could be carried out in such a medium, it is advantageous in certain cases, for the phase of condensation with the compound of aromatic nature, to dilute it with an aliphatic organic acid such as acetic acid in order to permit better dispersion and to add if necessary a little surface active agent. This condensation phase being carried out with the formation of water, it is obviously advantageous to use as concentrated a sulfuric acid as possible, and even in certain cases to add oleum to the sulfuric acid.

The separation of the final condensation product from the reaction medium is carried out by methods known in themselves and which are a function of the properties of this product and notably its water solubility.

When the final product is little soluble in water, it generally suffices to dilute the reaction medium with water in order to precipitate it.

Any other method of isolating the final condensation product by a known method is nonetheless usable departing from the scope of the invention.

Of course, it is possible from N-acyl derivatives of α-substituted glycines prepared by the method according to the invention, to obtain corresponding α-substituted glycines by deacylation by customary methods, for example, by heating with an aqueous hydrochloric solution.

Thus, as has been indicated above, the N-acyl derivatives of α-substituted glycines prepared by the process according to the invention or the corresponding α-substituted glycines are important intermediates in the manufacture of semi-synthetic penicillins.

DESCRIPTION OF PREFERRED EMBODIMENTS

The following examples are given purely by way of illustration of the invention and are not to be regarded as limiting.

EXAMPLE 1

N-acetyl-phenyl glycine

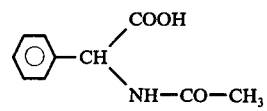

To 105g (1 mole) of 70% aqueous solution of glyoxylic acid, there is added 280 ml of approximately 96% sulfuric acid without exceeding 25° C, then 41 g (1 mole) of acetonitrile, keeping the temperature at 25°–30° C. It is left for 30 minutes at this temperature, then this solution is added slowly into 390 g (5 moles) of benzene with vigorous stirring keeping the temperature between 8° and 10° C. After the addition the temperature is allowed to rise to 25° C and kept thus for 15 hours.

The acid phase is run into 800 ml of cooled water thereby avoiding exceeding 30° C. After cooling to 0° C, it is filtered, washed with water and dried on a fluidised bed. 135 g of product is obtained namely a yield of 70% with respect to the glyoxylic acid. The product recrystallised from ethyl acetate melts at 199°–201° C and titrates 98.8% of the theoretical by acidimetry.

| Elementary analysis | Calculated | Found |
|---|---|---|
| C | 62.2% | 61.8% |
| H | 5.7% | 5.8% |
| N | 7.2% | 7.0% |

EXAMPLES 2, 3 AND 4

N-acetyl-phenylglycine

Procedure is as in Example 1, but with the addition of 60 g (1 mole) of acetic acid to the reaction solution of the glyoxylic acid with the acetonitrile before the addition of the benzene.

By keeping it for four and a half hours at 25° C, a yield of 57.5% of N-acetamido-phenylglycine is obtained with respect to the glyoxylic acid.

Keeping it now for 6½ hours at 25° C, one obtains a yield of 60.5% and by now keeping it for 18 hours at 25° C, one obtains a yield of 65.5%.

EXAMPLE 5

N-acetyl (4-chloro-phenyl) glycine

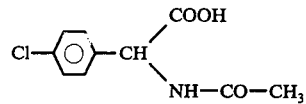

Procedure is as in Example 1 replacing the benzene by chlorobenzene and using molar amounts of reactants equal to half of those of this Example.

73 g of product, namely a yield of 64%, are obtained.

EXAMPLE 6

N-acetyl phenylglycine

Procedure is as in Example 1, but with 195 g (2 moles) of 76% glyoxylic acid, 560 ml of concentrated sulfuric acid, 82 g (2 moles) of acetonitrile and 760 g (10 moles) of benzene and a duration of only 6 hr. 15 min.

A yield of 73.5% was obtained. The recrystallised product melts at 200° C.

EXAMPLE 7

N-acetyl (4-methylphenyl) glycine

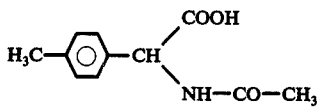

The procedure is as in Example 1, for a duration of 5 hr. 45 min. only with 181 g (2 moles) of 82% glyoxylic acid, 450 ml of concentrated sulfuric acid, 82 g (2 moles) of acetonitrile, 921 g (10 moles) of toluene. 12 of crystallisable acetic acid and 0.9 g of surface active agent are also added.

The acid phase is run into 1600 ml of water. It is filtered, washed thoroughly with water and dried. 240 g of crude product are obtained, namely a yield of 58%. The product recrystallised in nitromethane melts at 218°–222° C.

EXAMPLE 8

N-acetyl (2,4-dimethyl phenyl) glycine

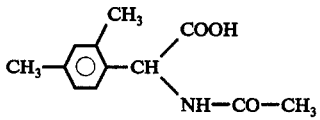

The procedure is as in Example 1 for a duration of 5 hr. 45 min. only with 185 g (2 moles) of 80% glyoxylic acid, 450 ml of concentrated sulfuric acid, 82 g (2 moles) of acetonitrile, 636 g (6 moles) of m-xylene. In addition, 120 g of crystallisable acetic acid and 0.6 g of surface active agent, are added.

The acid phase is run into 1600 ml of water. It is filtered, washed with water and dried. 270 g of white crude product are obtained, namely a yield of 61%. The crude product recrystallised in a water/ethanol 66/33 mixture, melts at 165°–172° C.

EXAMPLE 9

N-acetyl (2,5-dimethyl phenyl) glycine

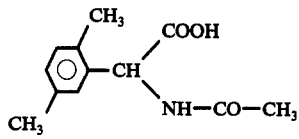

The procedure is as in Example 1, for a duration of 5 hr. 20 min. only with 174 g (2 moles) of 85% glyoxylic acid, 450 ml of concentrated sulfuric acid, 82 g (2 moles) of acetonitrile, and 636 g (6 moles) of paraxylene.

In addition, 120 g of acetic acid and 0.6 g of surface active agent are added.

The acid phase is run into 1600 ml of water. 280 g of dry crude product are obtained, namely a yield of 63.5%. The crude product melts at 216°–218° C.

We claim:

1. The process of manufacturing N-acyl derivatives of glycines alpha-substituted by aromatic radicals, comprising the steps of (a) reacting in the presence of concentrated sulfuric acid, at a temperature lower than or equal to about 30° C, an aliphatic nitrile of the formula R—C≡N in which R is a radical selected from the group consisting of substituted and unsubstituted, saturated and unsaturated alkyl radicals with a concentrated aqueous solution of glyoxylic acid; (b) condensing the mixture obtained from (a) at a temperature lower than or equal to about 35° C, with a substituted or unsubstituted aromatic hydrocarbon or thiophene derivative not having an hydroxyl group in its formula and having at least one substitutable free hydrogen and (c) collecting the resulting product.

2. The process according to claim 1 in which the concentrated sulfuric acid is supplemented with acetic acid during the phase of condensation with the substituted or unsubstituted aromatic hydrocarbon or thiophene derivative.

3. The process according to claim 1 in which a surface active agent is added in addition to the acetic acid during the phase of condensation with the substituted or unsubstituted aromatic hydrocarbon or thiophene derivative.

4. The process according to claim 1 in which nitriles comprising not more than four carbon atoms are used as the nitrile R—C≡N.

5. The process according to claim 1 in which the nitrile is selected from the group consisting of acetonitrile, chloracetonitrile, propionitrile, acrylonitrile and butyronitrile.

6. The process according to claim 1 in which as the compound with aromatic character there is used a compound selected from the group consisting of benzene, toluene, xylene, o-chlorobenzene, and thiophene.

* * * * *